(12) United States Patent
Uhlén et al.

(10) Patent No.: US 6,831,161 B1
(45) Date of Patent: Dec. 14, 2004

(54) METHOD OF AFFINITY SEPARATION AND LIGANDS FOR USE THEREIN

(75) Inventors: Mathias Uhlén, Täby (SE); Sophia Hober, Stockholm (SE)

(73) Assignee: Affibody AB, Bromma (SE)

( * ) Notice: Subject to any disclaimer, the term of this patent is extended or adjusted under 35 U.S.C. 154(b) by 0 days.

(21) Appl. No.: 09/830,080

(22) PCT Filed: Oct. 21, 1999

(86) PCT No.: PCT/GB99/03484
§ 371 (c)(1),
(2), (4) Date: Sep. 24, 2001

(87) PCT Pub. No.: WO00/23580
PCT Pub. Date: Apr. 27, 2000

(30) Foreign Application Priority Data

Oct. 21, 1998 (GB) .............................. 9823071

(51) Int. Cl.⁷ ................................ A07K 1/22
(52) U.S. Cl. ................... 530/413; 435/6; 435/7.1
(58) Field of Search ................ 530/413, 810, 530/811; 436/518; 435/6, 7.1

(56) References Cited
FOREIGN PATENT DOCUMENTS

WO   WO 95/19374   7/1995

OTHER PUBLICATIONS

Friedman, A. R.; Ichhpurani, A. K.; Brown, D. M.; Hillman, R. M.; Krabill, L. F.; Martin, R. A.; Zurcher–Neely, H.A.; Guido, D. M. 1991, Int. J. Peptide Protein Res. 37, 1991, 14–20.*
Carlsson, J, Janson, J–C and Sparrman, M: Protein Purification: Principles, High–Resolution Methods, and Applications, Second Edition, Chapter 10, pp. 375–442 (1998).
Nygren, P–Å and Uhlén M: Current Opinion in Structural Biology, vol. 7, pp. 463–369 (1997).
Nord, K et al: Protein Engineering, vol. 8, No. 6, pp. 601–608 (1995).
McBride, J D et al: Journal of Molecular Biology, vol. 259, pp. 819–827 (1996).
Schatz, P J: Biotechnology, vol. 11, pp. 1138–1143 (Oct., 1993).
Lu, Z et al: Biotechnology, vol.13, pp. 366–372 (Apr., 1995).
Clackson, T and Wells, J A: Trends in Biotechnology, vol. 12, pp. 173–184 (1994).
Boder, E T and Wittrup, K D: Nature Biotechnology, vol. 15, pp. 553–557 (Jun., 1997).
Ernst, W et al: Nucleic Acids Research, vol. 26, No. 7, pp. 1718–1728 (1998).
Grabherr, R et al: Biotechniques, vol. 22, pp. 730–735 (Apr., 1997).
Kraulis, P J et al: Federation of European Biochemical Societies, Letters 378, pp. 190–194 (1996).
Sthåhl, S et al: Journal of Immunological Methods, vol. 124, pp. 43–52 (1989).
Nilsson, J et al: European Journal of Biochemistry, vol. 224, pp. 103–108 (1994).
Nilsson, B et al: Protein Engineering, vol. 1, No. 2, 1987, pp. 107–113.
Gutte, B: Journal of Biological Chemistry, vol. 253, No. 11, Jun. 10, 1978, pp. 3837–3842.

* cited by examiner

Primary Examiner—Bennett Gelsa
Assistant Examiner—Jon D. Epperson
(74) Attorney, Agent, or Firm—Todd E. Garabedian; Wiggin and Dana LLP

(57) ABSTRACT

Methods of affinity separation wherein the affinity ligand is an immobilized proteinaceous ligand wherein one or more of its asparagine (Asn) residues has been modified. Methods of making a stabilized combinatorial protein by a) modification of Asn residues within a protein molecule to increase stability of the protein in alkaline conditions, and b) randomization of a protein molecule to modify its binding characteristics, and combinatorial proteins wherein in a step separate from the randomization step, the stability of the protein in alkaline conditions has been increased by modifying one or more of its Asn residues.

10 Claims, 7 Drawing Sheets

METHOD OF AFFINITY SEPARATION AND LIGANDS FOR USE THEREIN

CROSS-REFERENCE TO RELATED APPLICATIONS

This application is a §371 application of PCT/GB99/03484 filed Oct. 21, 1999.

BACKGROUND OF THE INVENTION

1. Field of the Invention
2. Discussion of the Related Art

The present invention relates to affinity separation and to ligands for use therein.

Affinity separations generally take place on an affinity chromatography column and take advantage of the potentially highly specific nature of interactions involving biomolecules, especially proteins. Other possible separation methods include membrane filtration, two-phase extraction, fluidised beds, expanded beds and magnetic bead separation (Scopes, R. K. Protein Purification, Principles and Practice, 3rd Ed. ISBN 0-387-94072-3). Interactions include protein-protein, protein-nucleic acid, enzyme-substrate, receptor-ligand (e.g. hormone) protein-carbohydrate and protein-metal interactions. Generally, affinity separation is based on the biologically important binding interactions that occur on protein surfaces, such as that between an enzyme and its substrate, between nucleic acid and a DNA binding protein or between antigen and antibody. Either one of a pair of binding partners can be immobilised, e.g. by covalent bonding to an insoluble matrix in an affinity column in order to assay for or purify its binding partner. The very selective nature of interactions between or involving affinity binding molecules, particularly proteins makes them ideal for purification/separation techniques and for many applications, affinity chromatography involving an immobilised protein ligand is preferred over ion-exchange or gel-filtration chromatography.

If a sample is added to a column which carries immobilised on a solid matrix a specific binding partner to a target molecule in the sample, the target molecule will be retained in the column while the majority of the non-target molecules will simply run through. A solution, typically containing a gradually decreasing pH can be added to the column to wash through firstly any non-specifically bound molecules and finally to elute the target molecule. The target molecule, having the highest affinity for the immobilised ligand, will be the last molecule to be washed off the column and it is therefore the final fractions which will contain the highest concentration of the target molecule and can then be used in a further purification/concentration step or be assayed directly or indirectly for the presence of the target molecule.

Medicine and research in the biochemical and biotechnological fields generally, has created a demand for ever purer samples of organic and biological molecules and thus for strategies which can provide samples of high purity as quickly and cheaply as possible.

As well as satisfying a need to obtain pure samples of proteins and other molecules, affinity separation is important in assaying samples quantitatively and qualitatively for a target molecule. This may be important, for example, when blood or urine samples are being assayed for molecules indicative of a disease such as a metabolic disorder or even the presence of non-naturally occurring substances, narcotics, steroid derivatives etc.

An affinity chromatography column, complete with its solid affinity matrix, can be expensive and clearly it is desirable to be able to re-use the column several times, i.e., to complete a number of runs before it has to be discarded due to reduced ability of the immobilised ligand to bind a target molecule or to a reduced specificity of binding. In order to achieve a set of results which can be directly compared and to clear the column of non-specific and specifically bound molecules before performing another run, it is necessary to clean the column. The recognised standard for cleaning and sanitizing separation media and systems is NaOH, often in combination with NaCl. An applied 0.1–1.0 M NaOH solution is able to remove viruses, bacteria, nucleic acid, proteins, yeasts, endotoxins, prions and other contaminating agents. The NaOH contact time may vary, between 30 minutes and 1 hour is typical, and removal from the system is monitored by simple in-line pH and conductivity measurements.

However, the ability of the separation media to withstand these rather harsh sanitizing conditions depends on the functional groups of the attached ligand (binding partner), attachment chemistries, and the stability of the base matrices to alkaline conditions. Proteins are sensitive to extreme pH, such as is experienced during NaOH cleaning and, generally speaking, this will adversely affect the effectiveness of protein-based affinity media. Thus, although protein based affinity separation has advantages over ion exchange and gel-filtration chromatography due to its good specificity, these other less specific techniques are not adversely affected by standard cleaning methods.

The sensitivity of proteins to alkaline pH is primarily due to deamidation of asparagine and glutamine residues, particularly asparagine residues. Deamidation of asparagine results in the formation, via a cyclic imide intermediate, of isoaspartate and aspartate, usually in the ratio of 3:1 to 4:1. This reaction does take place at physiological pH but is far faster at alkaline pH such as present in a chromatography column which is being cleaned by an NaOH solution. The isoaspartyl form is characterised by an atypical amide bond between the β-carboxyl of aspartate and the α-nitrogen of the C-flanking amino acid. This results in an extra —$CH_2$— in the backbone of the protein as well as a free α-carboxyl group. Cleavage of the peptide backbone may occur as a result of the deamidation and the protein may lose its activity due to a structural change in the whole protein, or merely a small change in a sensitive region such as the active or binding site. The susceptibility of asparagine residues to deamidation is sequence and conformation dependent, Asn residues at Asn-Gly and Asn-Ser sites being particularly vulnerable.

It is a serious problem when an affinity chromatography column has been set up with a protein immobilised on an insoluble support within it and the necessary cleaning process between runs results in reduced efficacy of the system. As well as hastening the end of the absolute useful life of the column, if successive washes decrease the ability of the immobilised protein to capture its binding partner from a sample, comparisons between runs where the concentration of an analyte in a series of samples is measured become meaningless. There is therefore a need for a method of affinity separation wherein the immobilised protein is less susceptible to standard cleaning methods, particularly to alkaline pH.

OBJECTS AND SUMMARY OF THE INVENTION

Thus, in one aspect, the present invention provides a method of affinity separation wherein the affinity ligand is an immobilised proteinaceous ligand wherein one or more of its asparagine residues has been modified.

The term "modified" includes deletion of the asparagine residue or replacement of it with a less alkaline-sensitive amino acid, or wherein the asparagine residue has been modified by substitution (i.e. chemical substitution of one or more groups) or other chemical derivitisation, e.g. by a protecting group. Replacement of one or more asparagine residues with a less alkaline-sensitive amino acid is preferred.

By 'affinity separation' is meant any purification or assaying technique which involves the addition of a sample containing a target analyte to a solid which carries on it a specific binding partner to the analyte.

Gravity or other means allows the sample to pass through or across the solid, and the interaction between the analyte and its specific binding partner immobilised on the solid means that the analyte will be retained on the solid while the rest, or most of the rest, of the sample passes through the system. The separation may conveniently be carried out on an affinity chromatography column. The solid is preferably arranged in a column, so that the sample can be added to the top and the non-target part of the sample runs off. An eluant such as a salt solution or a change of pH can be used to displace the specifically bound analyte which can then be collected in a number of aliquots in a controlled manner.

An "affinity ligand" is thus a target-specific binding partner, which can be used in an affinity separation process.

'Analyte' is used to refer to any molecule or fragment of a molecule, proteinaceous or otherwise, in a sample which is capable of binding specifically to the immobilised ligand.

The term 'specific binding partner' may include a molecule or a group of related molecules and any one of these molecules may also bind 'specifically' to one or more other molecules. Thus, the term does not imply that any one immobilised ligand or analyte can have only one binding partner, rather that binding is specific to the extent that most other molecules will not bind with the same affinity or with the same stringency, particularly that other non-target molecules in a given sample will have a much lower affinity. Purification by affinity separation is often of the order of several thousand-fold because of the high affinity between biologically specific binding partners.

All types of affinity separation which include an immobilised proteinaceous ligand can be used in the method of the invention, and suitable matrices (i.e. solid support) known for use with particular ligands are known in the art, typically based on chromatography using agarose, polacrylamide, silica, polyvinyl styrene, dextran or other polymers. Any of the solid support known in the art for separation or immobilisation processes may be used, as indeed may any of the methods known in the art for attaching molecules such as affinity ligands to solid supports. The proteinaceous ligands are usually attached to the matrix by a coupling agent such as cyanogen bromide, epichlorohydrin, bisoxirane, divinyl sulfone, carbonyl diimidazol, N-hydroxysuccinimide, tosyl/tresyl chloride, epichlorohydrine, carbodiimide, glutaraldehyde, hydrazine, oxirane and also carboxyl or thiol activated matrices and again such coupling agents and coupling chemistries are well known in the art and widely described in the literature (Jansson, J. C. and Rydén, L. Protein purification, 2nd Ed. pp 375–442, ISBN 0-471-18626-0). Various derivatives of matrices which allow straightforward immobilization include CNBr-activated Sepharose 4B, AH-Sepharose 4B and CH-Sepharose 4B and Epoxy-activated Sepharose 6B (Pharmacia).

The proteinaceous affinity ligand may be a molecule having a protein component, which may function as a "specific binding partner" as defined above. Thus, glycoproteins or protein-lipid complexes or indeed proteins with prosthetic groups may be used as the affinity ligand which is modified according to the present invention. Protein molecules are, however, preferred. The term "protein" is used herein broadly to include any molecule having a polypeptide or peptide structure. In other words, as used herein, a "protein" is made up of a chain of amino acids, and the term does not imply any particular conformational (i.e. tertiary structure) or other requirement.

Suitable amino acids to replace asparagine include any of the other 19 standard naturally occurring amino acids, although cysteine and glutamine would not be preferred. Preferred substituting amino acids include lysine, aspartic acid and leucine. Non-naturally occurring amino acids and amino acid derivatives which are well known to the man skilled in the art could also be used to replace asparagine residues. Significant improvements in the stability of the immobilised protein and thus the efficacy of the column after cleaning can be observed when just one asparagine is substituted by a less alkaline sensitive residue but preferably 2, 3 or more, or even all of the asparagine residues are substituted.

A "less alkaline-sensitive amino acid" is one which is less susceptible to degradation under alkaline conditions than Asn, when compared using techniques, methods and conditions known in the art. Such conditions may, for example, be the column washing conditions discussed above, or any other alkaline conditions used in the art to study protein stability or degradation e.g. deamidation as discussed above. A "less alkaline-sensitive" amino acid may thus be any amino acid other than Asn, and more preferably other also than Gln and Cys. Conveniently, alkaline-sensitivity may be compared by replacing a given Asn residue in a protein molecule with a substitute amino acid, or by chemically modifying or derivatising the said Asn residues, and then comparing stability in alkaline conditions (e.g. column wash conditions) with the unmodified protein.

As indicated above, the sensitivity of a particular asparagine residue to deamidation will depend on the configuration of the protein, it being particularly important to replace those residues which are on the surface of the three dimensional structure of the protein and thus particularly exposed to the alkaline conditions. It is the overall stability of the ligand which is of most importance and it is desirable to retain the specificity of the interaction between the immobilised ligand and its binding partner, therefore, preferably it is the asparagine residues not involved in the ligand-analyte interaction which are replaced.

The "asparagine modified" proteinaceous affinity ligand (hereinafter the "modified protein") may be made by any method known to the skilled man. Standard techniques for site-directed mutagenesis of nucleic acids are described, for example, in the laboratory manual entitled Molecular Cloning by Sambrook, Fritsch and Maniatis. A preferred technique involves PCR mutagenesis, where primers which incorporate the necessary mis-match base pairs to generate the desired mutations are used in a first round of PCR. In the second run, the fragments from the first run are mixed and the polymerase is able to fill in the strands. The resulting double stranded fragment can be ligated into a plasmid which is then used to transform E. coli. The protein can by synthesised in vitro without using a biological host and in this case non-naturally occurring amino acids can be introduced.

As well as the many general uses of affinity separation indicated previously, of particular interest in the present case is the use of affinity separation with ligands which have been made by randomisation (random mutagenesis) of a particular protein to generate ligands with novel, modified or enhanced binding characteristics. These proteins are referred to as combinatorial proteins. Such a technique typically involves random mutagenesis of a target protein, expression of the full library of these variants, e.g. on the surface of filamentous bacteriophage, followed by selection of a protein exhibiting the desired binding characteristics, this selection typically involving a binding reaction between the variant protein and an immobilised ligand (binding partner) i.e. target molecule for the protein, e.g. target analyte. The mutagenesis is random in that the resulting amino acid encoded by any particular codon is not generally predetermined but the positions where mutations are to be introduced are generally identified in advance. The mutagenesis may involve amino acid substitution deletion, or addition (e.g. insertion).

The use of an expression system such as surface display on phage provides a crucial link between genotype and phenotype; there is a self-contained unit which can be selected on the basis of its specific binding interactions and which also carries the nucleic acid encoding for the protein responsible for the observed binding characteristics. This enables expression in useful amounts of the protein selected for its binding characteristics, such expression typically taking place in a transformed bacterial host.

The protein, selected by its ability to bind to an immobilised ligand (e.g. a desired target molecule (analyte)), is then itself used in affinity separation (i.e. as the affinity-ligand). It is immobilised and used to purify or assay for a target molecule in a sample, typically the same ligand which was used to select the protein in the first place. In this way, a protein from a library of variants can be selected for its ability to bind e.g. insulin, using a column with insulin immobilised on a matrix therein and the selected protein can then be used to test samples for the presence of insulin.

As well as testing for the presence of a target molecule, the affinity separation methods of the invention provide excellent purification methods, yielding samples of a target molecule having good purity. In particular, the methods of the invention will still produce pure samples after many cycles of the separation system, e.g. after many runs, with washing, of a column. Such samples produced by the methods of the invention constitute further aspects of the invention.

If a protein is stabilised by replacing one or more of its asparagine residues with a less alkaline sensitive amino acid prior to the randomisation and selection steps described above, then its useful life as an affinity ligand will be extended due to its ability to withstand the harsh conditions such as high pH which are experienced when an affinity column is washed between runs.

Therefore, a further aspect of the present invention comprises a combinatorial protein wherein in a step separate from the randomisation step (i.e. the step used to generate the combinatorial protein by randomisation of an "origin" or "source" or "starting protein"), the stability of the protein in alkaline conditions has been increased by modifying one or more of its asparagine residues (preferably by replacing one or more of its asparagine residues with a less alkaline sensitive amino acid).

Nucleic acid molecules encoding such a protein as well as cells expressing the protein constitute further aspects of the present invention.

The randomisation may itself result in substitution of asparagine residues but this aspect of the invention is concerned with proteins which have also been specifically modified to replace one or more asparagine residues in order to increase stability. The protein can be stabilised before or after the randomisation or at the same time but preferably the stabilising modifications will be introduced before the randomisation takes place. If stabilisation is performed before randomisation, it need only be performed once, and by selecting from the library of randomised variants against a number of ligands, several stabilised proteins with different binding characteristics can be obtained. If the stabilisation is performed after selection for a particular binding affinity, then there is a risk that some affinity would be lost as a result of the stabilising substitutions.

Techniques for construction of a combinatorial library of protein molecules and subsequent selection to obtain proteinaceous ligands having desired binding characteristics are known in the art (Nygren, P. and Uhlén, M. Current Opinion in Structural Biology (1997) 7: 463–469). Generally, a protein molecule, perhaps having intrinsic beneficial properties such as temperature or pH insensitivity, is used as a scaffold and a combinatorial library is then constructed via random but targeted amino acid substitutions (or other mutations) of that protein molecule, in order to produce a library of molecules having different binding characteristics. Surface residues are generally targeted for random mutagenesis.

Suitable protein scaffolds may simply be linear peptides but preferably the scaffold will possess a folded three dimensional structure which has the potential for higher affinities and is less susceptible to proteolytic degradation. Rather than designing a scaffold de novo, naturally existing proteins or domains are usually selected for further engineering. For the avoidance of doubt, it is to be noted that throughout this specification the word "protein" is used to refer to whole protein molecules as well as domains or fragments thereof, polypeptides or peptides. The choice of protein scaffold depends on several parameters including an ability to be effectively expressed in a desired host organism e.g E. coli when the randomised protein is to be displayed as a fusion protein with a filamentous phage coat protein. The protein should also comprise sufficiently large regions on its surface which are tolerant to substitution (or insertion or deletion etc.) without losing the overall three dimensional structure. If the library is to be produced synthetically, a small overall size is a prerequisite. Where the selected scaffold protein has a binding function, amino acid residues involved in that interaction may be a target for randomisation. Randomisation may be performed in order to enhance known binding properties or to develop ligands with new specificities.

Suitable scaffold molecules are discussed in Nygren et al. (1997) and include cyclic peptides having 40 or more residues in a constrained sequence, immunoglobulin-like scaffolds including Fv or single-chain (scFv) domains, bacterial receptors such as the 58-residue one-domain Staphylococcal protein A (SPA) analogue Z (the "Z Domain" being a derivative of the B domain of SPA), or other domains or analogues of SPA, DNA-binding proteins particularly zinc fingers and protease inhibitors. All these molecules can be stabilised by substituting one or more native asparagine residues with a less alkaline sensitive amino acid before a combinatorial library of the pre-stabilised protein is made.

Of particular interest is the bacterial receptor domain Z (Nord, K., Nilsson, J., Nilsson, B., Uhlén, M. and Nygren, P. Protein Engineering (1995) 8, 6, 601–608). This paper by Nord et al. describes a suitable method of constructing a combinatorial library of protein molecules which can be applied to a range of scaffold molecules. The method described is solid-phase-assisted and based on the stepwise assembly of randomised single-stranded oligonucleotides.

Selection from a generated protein library can be performed in a number of different ways known in the art, including bead immobilised libraries (McBride, J. D., Freeman, N., Domingo, G. J. and Leatherbarrow, R. J., J. Mol. Biol. [1996] 259: 819–827), fusions to DNA-binding proteins (Schatz, P. J., Biotechnology [1993] 11, 1138–1143) and when displayed on bacteria (Lu, Z., Murray, K. S., Van Cleave, V., LaVallie, E. R., Stähl, M. L. and McCoy, J. M. Biotechnology [1995], 13 366–372) or phage (Clackson, T. and Wells, J. TIBTECH (1994) 12, 173–183) as well as yeast cells, (Boder, E. T. and Wittrup, K. D., Nature Biotechnology (1997) 15, 553–557) and in viral systems (Ernst, W., Grabher, R., Wegner, D., Borth, N., Graussauer, A. and Katinger, H. Nucleic Acids Research (1998) 26, 1718–1723 and Grabher, R., Ernst, W., Doblhoff-Dier, O., Sara, M. and Katinger, H. BioTechniques (1997) 22, 730–735).

International Patent Application, publication No. WO 95/19374 describes the generation of a combinatorial library of Z-variants, see in particular Example 4. This application discusses on page 12 the advantages of the Z domain as an affinity ligand in the purification of recombinant proteins, as it is relatively stable in the harsh environment of an affinity column during cleaning. The present invention offers further benefits in that the Z domain can be stabilised to alkaline pH by replacement of asparagine residues. According to the present invention it is proposed to stabilise the native Z domain before the combinatorial library is prepared.

Thus in a further aspect, the present invention provides a method of preparing a combinatorial library of protein molecules wherein the protein has been rendered less sensitive to alkaline pH by modification of one or mote of its asparagine residues before it is randomised (preferably by replacement of one or more of its asparagine residues).

In a yet further aspect of the present invention is provided a method of phage display wherein a protein expressed on the phage surface has had one or more of its asparagine residues modified (preferably by replacement with a less alkaline sensitive residue) in a step separate to any modifications introduced in order to modify binding characteristics of the protein.

A further aspect of the present invention comprises a method of making a stabilised combinatorial protein comprising the steps of:
a) modification of asparagine residues within a protein molecule to increase stability of the protein in alkaline conditions; and
b) randomisation of the protein molecule to modify its binding characteristics.

Modification in step a) will preferably comprise replacement of asparagine residues with other less alkaline sensitive amino acids, Step a) is preferably carried out before step b).

As well as a protein molecule which has been randomised and stabilised, the present invention also relates to fusion proteins comprising a stabilised part and a randomised part, such proteins being useful in certain applications. In particular, this technique enables the development of a stable framework which can have attached thereto a variable region with specific binding characteristics. The variable region can be prepared by randomisation techniques as discussed above and a protein molecule having desired binding characteristics can be selected from the library of variants, for example by phage display and affinity chromatography. This randomised protein can then be expressed as a fusion protein, e.g. in E. coli, together with a protein molecule which has already been engineered to improve its stability to alkaline conditions by replacing one or more of its asparagine residues with other less alkaline sensitive residues.

The fusion protein can be used as an immobilised ligand in affinity chromatography, giving the benefits of a generally stable molecule provided by the framework part as well as a pre-selected binding affinity provided by the randomised part. Such a system may enable the use of a small protein molecule during the randomisation and selection stage as important protein-like characteristics (as opposed to peptide characteristics) are provided by the stabilised part. The same stabilised part can be used together with a variety of different randomised molecules and vice versa. Suitable protein molecules to perform as the stabilised framework part of the fusion peptides include Albumin Binding Protein (ABD); the bacterial receptor domain Z is a suitable molecule for randomization in this context.

Thus the present invention also provides a fusion protein comprising a first part wherein one or more naturally occurring asparagine residues have been modified (preferably replaced by an amino acid residue less sensitive to high pH) and a second part being a randomised protein molecule selected for its specific binding properties.

Nucleic acid molecules encoding such a protein as well as cells expressing the protein constitute further aspects of the present invention.

A further aspect of the present invention comprises a method of stabilising an affinity ligand by modifying one or more of its asparagine residues (preferably the affinity ligand is stabilised by replacing one or more of its asparagine residues with an amino acid residue less sensitive to alkaline pH).

A still further aspect comprises the use of a protein molecule stabilised by modification of one or more of its asparagine residues in surface display or in affinity chromatography.

The term 'surface display' refers to the technique involved in selection of a protein from a library of molecules which are presented (displayed) in a manner which enables differentiation between the protein molecules on the basis of their binding characteristics.

Surface display is typically performed on the surface of filamentous bacteriophage (phage display) but display can also be on the surface of bacteria, yeast cells or using viral systems. Any "surface display" technique known or proposed in the art, may be used according to the present invention.

A preferred affinity ligand for use in the methods of the invention is Albumin Binding Protein (ABD), a protein domain with affinity towards human serum albumin (HSA). It is derived from a cell wall anchored bacterial receptor protein from Streptococcus G148. It is of particular use as an affinity ligand for the purification of human serum albumin (HSA). The wild type sequence of this protein has four asparagine residues, enhanced stability is observed when just one of these residues is substituted but preferably all four residues are replaced by less alkaline sensitive residues. The wild type amino acid sequence of ABD is:
LAEAKVLANRELDKYGV-
SDYYKNLINNAKTVEGVKALIDEILAALP
the asparagine residues have been indicated in bold. The hyphen simply indicates that other molecules in the same family have an additional amino acid in this position. This sequence excludes the 19 amino acid N-terminal 'tail' shown in FIG. 3. Throughout the text particular amino acids of ABD are identified by their position in the full sequence (including the 19 amino acid 'tail') as presented in FIG. 3. Thus, the first asparagine residue of ABDwt which may be stabilised is in position 28 ($Asn_{28}$). Stabilised versions of ABD for use in the methods of the invention may incorporate some, all or none of the 19 amino acid N-terminal tail.

Stabilised ABD may, as discussed above, be further subjected to randomisation to create a protein (i.e. a combinatorial protein) having e.g. modified binding characteristics for HSA and/or that is able to bind any target of choice and also retains affinity towards HSA.

The randomisation may involve mutagenesis of the same, or preferably different, residues modified in the stabilisation step. Such derivatives of ABD (e.g. mutants created by random or directed mutagenesis) are also included within the scope of the invention.

Thus a further aspect of the present invention is Albumin Binding Protein (ABD) or fragments or derivatives thereof wherein one or more native asparagine residue have been replaced by a less alkaline sensitive amino acid. Nucleic acid molecules encoding such a protein as well as cells expressing the protein constitute further aspects of the present invention.

In a particularly preferred embodiment $Asn_{28}$ is replaced by leucine, $Asn_{42}$ by aspartic acid, $Asn_{45}$, by aspartic acid and $Asn_{46}$ by lysine (referred to as ABDmut herein). 'ABDmut' is used to refer to proteins incorporating some, all or none of the 19 amino acid N-terminal tail. Typically, if ABDmut is part of a fusion protein, e.g. with domain Z, then only part or none of the N-terminal tail will be present. Asparagine is the most alkaline sensitive amino acid and so any other amino acid residue could be used to replace it and an increase in stability would be expected. It may be of assistance to compare the sequences of other homologous proteins, which are found in other species or perform the same role, to identify suitable amino acids to be used in the substitution.

In a method suitable for the stabilisation of other affinity ligands, the modifications were introduced by PCR mutagenesis. Firstly mismatched primers are used to introduce the mutations and then the fragments from the first run of PCR are mixed and the polymerase allowed to fill in the strands. The double stranded fragment of ABD incorporating the modifications is cleaved with restriction enzymes and ligated into a plasmid restricted with the same enzymes, which is then used to transform *E. coli*, the expression system for the protein.

Preferably, the affinity ligand purified (i.e. obtained) according to the methods of the invention retains more than 80%, preferably more than 95%, of its normal binding capacity after 20 rounds of treatment with 0.5M NaOH.

DESCRIPTION OF THE DRAWINGS

The invention will be further described in the following non-limiting Examples in which.

Throughout the Examples ABDstab and ABDmut are used synonymously.

DESCRIPTION OF THE PREFERRED EMBODIMENTS

EXAMPLE 1

Cloning

Figure 1:
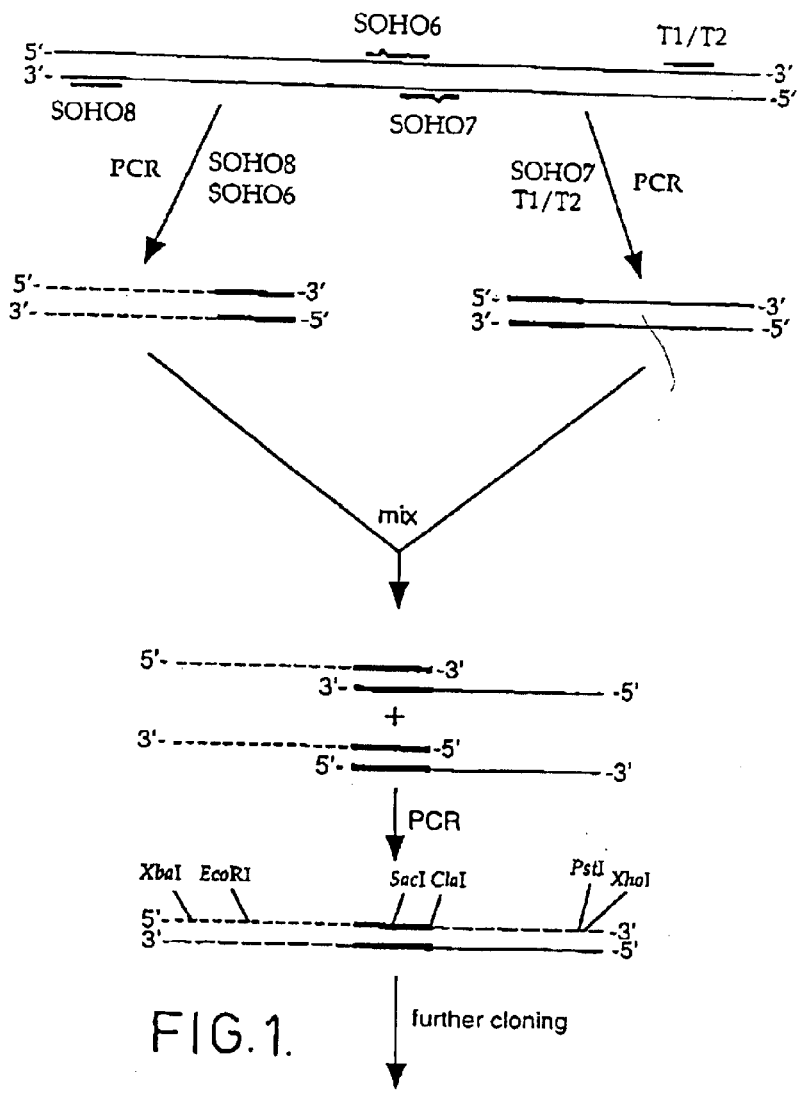
FIG. 1 is a schematic description of the PCR-mutagenesis step according to the invention.

As a template for the PCR mutagenesis pTrpABDT1T2 was used (Kraulis et al. (1996) FEBS Lett. 378, 190–194). The plasmid encodes the gene for ABDwt under control of the tryptophan promoter. The PCR mutagenesis was performed in two steps. In the first PCR the mutations was introduced and in the second round of PCR, the fragments from the first run were mixed and the polymerase was allowed to fill in the strands (FIG. 1). The primers used in the first PCR were:

5'-ACGTAAAAAG GGTATCTAGA ATTATGAAAG C-3' (SOHO8)(SEQ ID NO. 2)

3'-CAGAATCGAG ACTCTCTCGA GCTGTTTATA CC-5' (SOHO6)(SEQ ID NO. 3)

5'-GAGAGAGCTC GACAAATATG GAGTAAGTGA CTATTACAAG GATCTAATCG ATAAAGC-3' (SOHO7)(SEQ ID NO. 4)

3'-CCGCCTACTC TCTTCTAAAA GTCG-5' (T1T2)(SEQ ID NO. 5)

Figure 2:
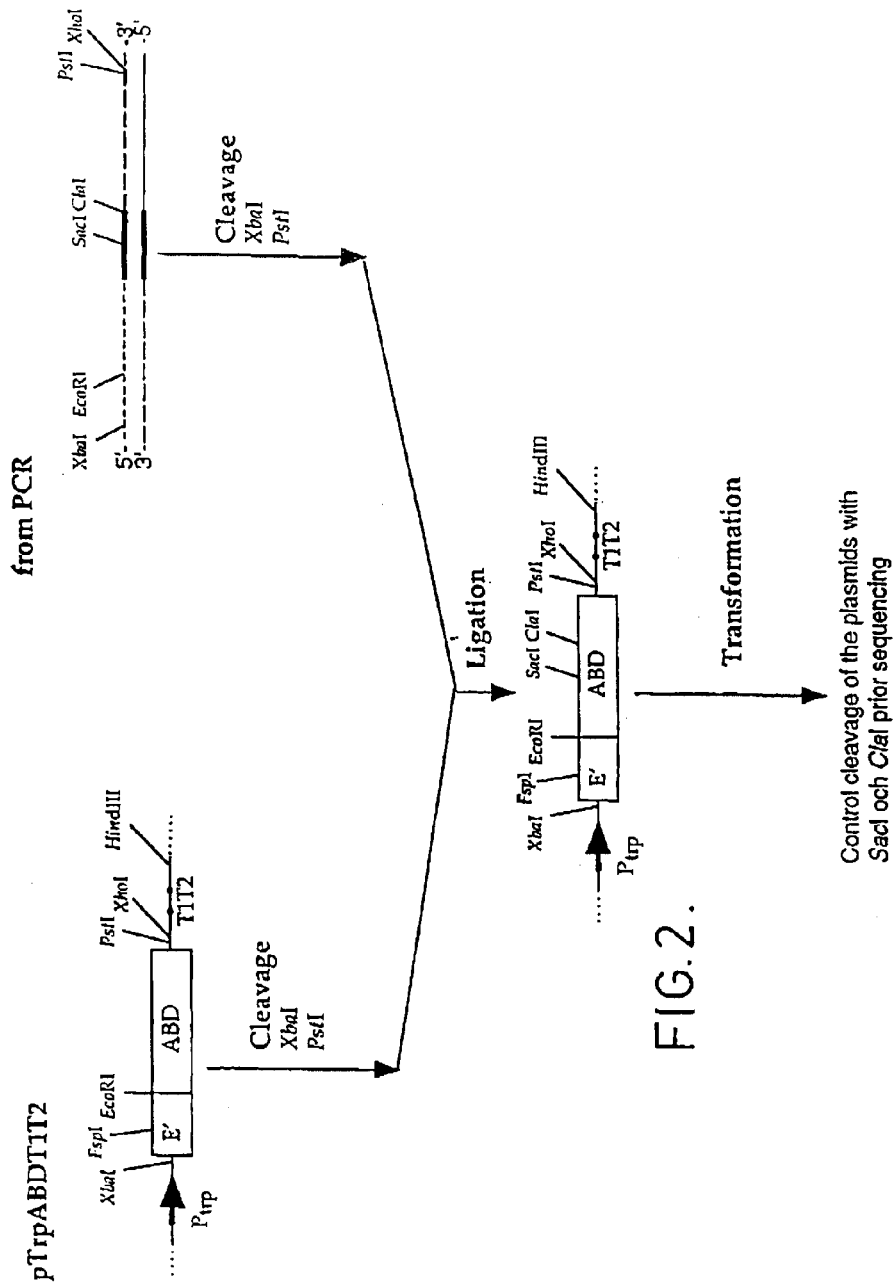
FIG. 2 shows the cloning of the gene construct.
Figure 3:
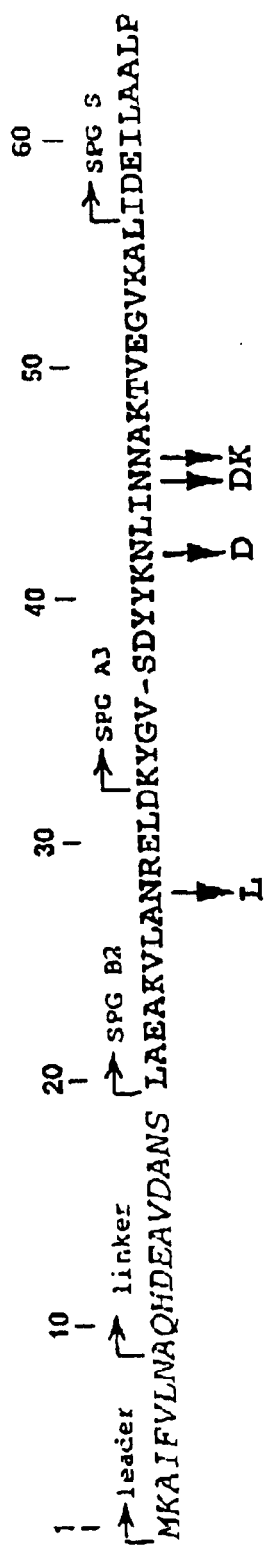
FIG. 3 is the amino acid sequence of wild type ABD and a mutated alkaline resistant variant of it, the full sequence of the mutated variant is designated herein as SEQ ID NO. 1.

The double stranded fragment was cleaved with Xba I and Pst I and ligated in to pTrpABDT1T2 restricted with the same enzymes (FIG. 2). The ligation mixture was used to transform *E. coli*, strain RRIΔM15. After confirming the size of the inserts by PCR, the sequence was verified by cycle sequencing (Amersham Pharmacia Biotech, Uppsala, Sweden). The resulting plasmid was denoted pTrpABDmutT1T2.

EXAMPLE 2

Expression and Purification

*E. coli* cells harboring the plasmid encoding ABDmut and also the wild type ABD as a reference were grown over night in shake flasks containing 500 ml Tryptic Soy Broth (30 g/l) supplemented with yeast extract (Difco, USA) (5 g/l) and kanamycin monosulphate (50 mg/l). Since the ABD gene is under control of the tryptophan promoter, the m-RNA production starts when the amino acid is missing in the growth medium. Cells were harvested after 20 hours by centrifugation, 4000×g in 10 minutes. After resuspending the cells in 30 ml TST (25 mM Tris-HCl, pH 7.5, 150 mM NaCl, 0.05% Tween 20) they were fractured by sonication. After that a centrifugation step was performed, approximately 40,000×g in 20 minutes. The supernatant was filtered (0.49 μm). The soluble protein was isolated by affinity chromatography on human serum albumin (HSA) Sepharose as described by Stahl et al. (1989) J. Immunol. Meth. 124, 43–52. The protein content in eluted fractions was measured by absorbance at 280 nm and relevant fractions were collected and lyophilized. Both proteins are of high purity after a single step purification and migrate in accordance with their molecular masses.

EXAMPLE 3

Binding Characteristics Before and After NaOH-treatment

Figure 5:
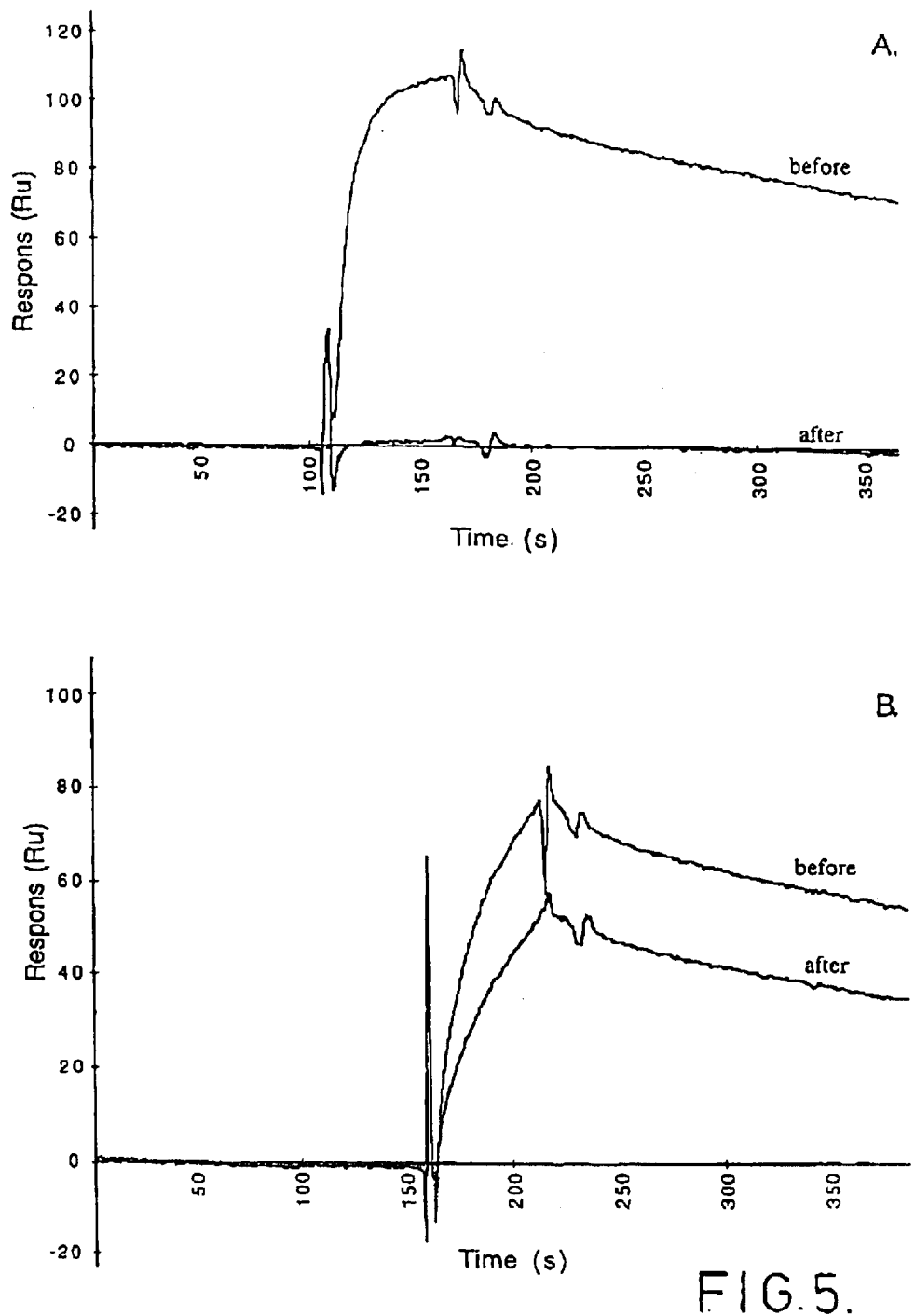
FIG. 5 shows Sensorgrams from the BIACore showing the binding characteristics of (A)ABDwt and (B)ABDmut before and after treatment with 0.5M NaOH for 24 hours.

In order to examine the stability of ABDwt and ABDmut, the binding characteristics were analysed before and after treatment with 0.5 M NaOH in room temperature for 24 hours. Both ABDwt and ABDmut were solubilized in 1×HBS (10 mM HEPES, pH 7.4, 150 mM NaCl, 3.4 mM EDTA, 0.005% P20) to a concentration of 800 nM and analyzed on BIAcore 2000 (Biacore AB, Uppsala, Sweden). In order to determine the activity change after exposure to a very alkaline environment, the proteins were solubilized in 0.5 M NaOH. After incubation in NaOH for 24 hours, the samples were run through a NAP-10 column (Amersham Pharmacia Biotech, Uppsala, Sweden) equilibrated with 30 mM NH$_4$Ac. The protein containing samples were lyophilized and resolubilised in 1×HBS to a concentration of 800 nM in order to be analyzed in the BIAcore 2000.
BIAcore Analysis A BIAcore 2000 instrument (Biacore AB) was used for real time affinity analysis. HSA and IgG were immobilized on two different surfaces of a CM5 sensor chip by amine coupling to the carboxylated dextran layer. This coupling was done according to the manufacturer's recommendation (Biacore AB). The IgG surface was used as a control. The samples were run through a 0.45 μm filter and injected over the surface in a random order at a flow rate of 5 μ/min. The results clearly show that ABDwt loses the affinity towards HSA during exposure to alkaline solution whereas the mutated variant that lacks four asparagine residues, has the affinity preserved. The sensorgrams are shown in FIG. 5.

Also, an analysis of the kinetic parameters was performed for the proteins that still remained active. This was done by analysing the binding behaviour in different concentrations and thereafter calculating the binding constants by using BIAevaluation 2.1 software (BIAcore AB). The concentrations used were 40–220 nM for ABDwt, 200–600 nM for ABDmut and 800–1250 nM for the NaOH treated ABDmut. The results are shown in table 1 below.

TABLE 1

|  | $K_{on}$ (1/Ms) | $K_{off}$ (1/s) | $K_{aff}$ (1/M) |
|---|---|---|---|
| ABDwt | $9.0 \times 10^4$ | $1.3 \times 10^{-3}$ | $6.9 \times 10^7$ |
| ABDmut | $1.8 \times 10^4$ | $1.2 \times 10^{-3}$ | $1.5 \times 10^7$ |

$K_{on}$ represents the rate at which the proteins associate, $K_{off}$ the dissociation rate and $K_{aff}$ is the affinity constant which is calculated as the ratio between $K_{on}$ and $K_{off}$.

EXAMPLE 4

Preparation of Affinity Matrices

In order to evaluate the usability of the stabilized HSA-binding protein in biotechnology, two affinity chromatography matrices were prepared; one with the unmutated protein (ABDwt) as a control and the other with the mutated ABD (ABDmut). The matrix used was Sepharose 4B (Amersham Pharmacia Biotech, Uppsala, Sweden) with carbodiimide CMC (Sigma Aldrich, Sweden) as the coupling reagent. ABDwt (4.5 mg) and ABDmut (8.5 mg) were dissolved in 9 ml water separately. 3.5 and 5.0 ml gel was added to ABDwt and ABDmut solutions respectively. Finally 0.38 g of CMC was added to the solutions and they were incubated at room temperature over night. The gels were packed on HR columns (d=5 mm, h=43 mm) and pulsed with 0.5 M ethanolamine, 0.5 M NaCl, pH 8.3 in order to inactivate the matrix and 0.1 M NaAc, 0.5 M NaCl, pH 4 in order to wash unbounded proteins out. After this, the columns were ready to use for affinity purification of HSA.

EXAMPLE 5

Retained Selectivity

Figure 4:
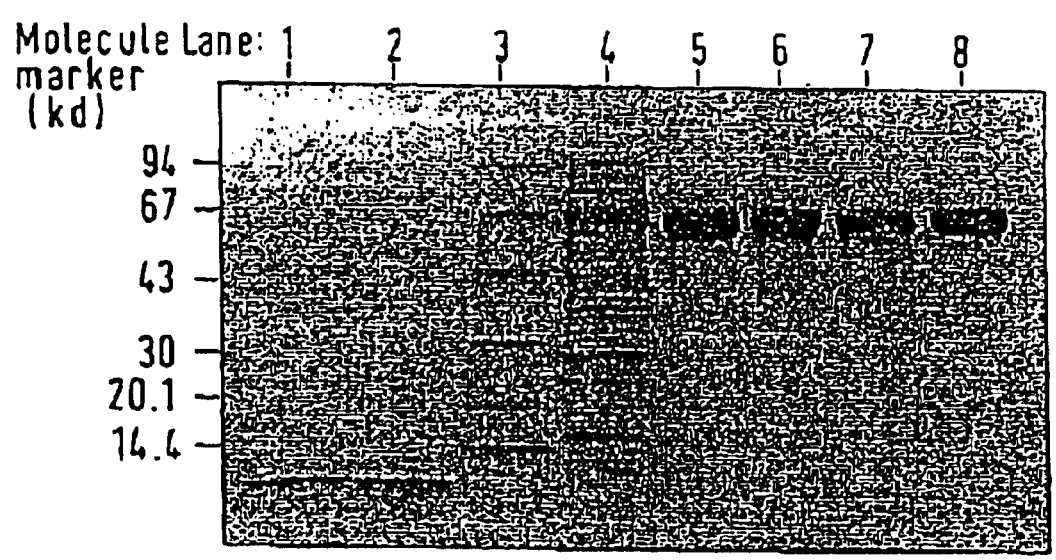
FIG. 4 shows an SDS-PAGE (4–20%) under reducing conditions. Lanes 1 and 2 show purified ABD and ABDstab respectively. The third lane shows a molecular weight marker (from top 94, 67, 43, 40, 20.2 and 14.4 kDa respectively). In order to check the selectivity of the mutated ABD, *E. coli* disintegrate was spiked with HSA (lane 4) and loaded onto the column. Lanes 5, 6 and 7 show the eluted material after 2, 8 and 15 rounds of NaOH treatment. Lane 8 shows an HSA reference.

To investigate if the selectivity of the mutated protein towards HSA was retained after exchanging four amino acids, a capture experiment was done. A culture of E. coli cells grown over night was fractured by sonication, centrifuged at 40,000×g and filtered through a 0.45 μm filter. The soluble fraction of the E. coli lysate was mixed with pure HSA and the mixture was applied on the ABDmut affinity column. After washing the column, the bound material was eluted by lowering the pH to 2.8 as described by Stahl et al., (1989) supra. As can be seen in FIG. 4, the selectivity is retained in the mutated variant of ABD.

EXAMPLE 6

Alkaline Resistant Affinity Columns

Figure 6:
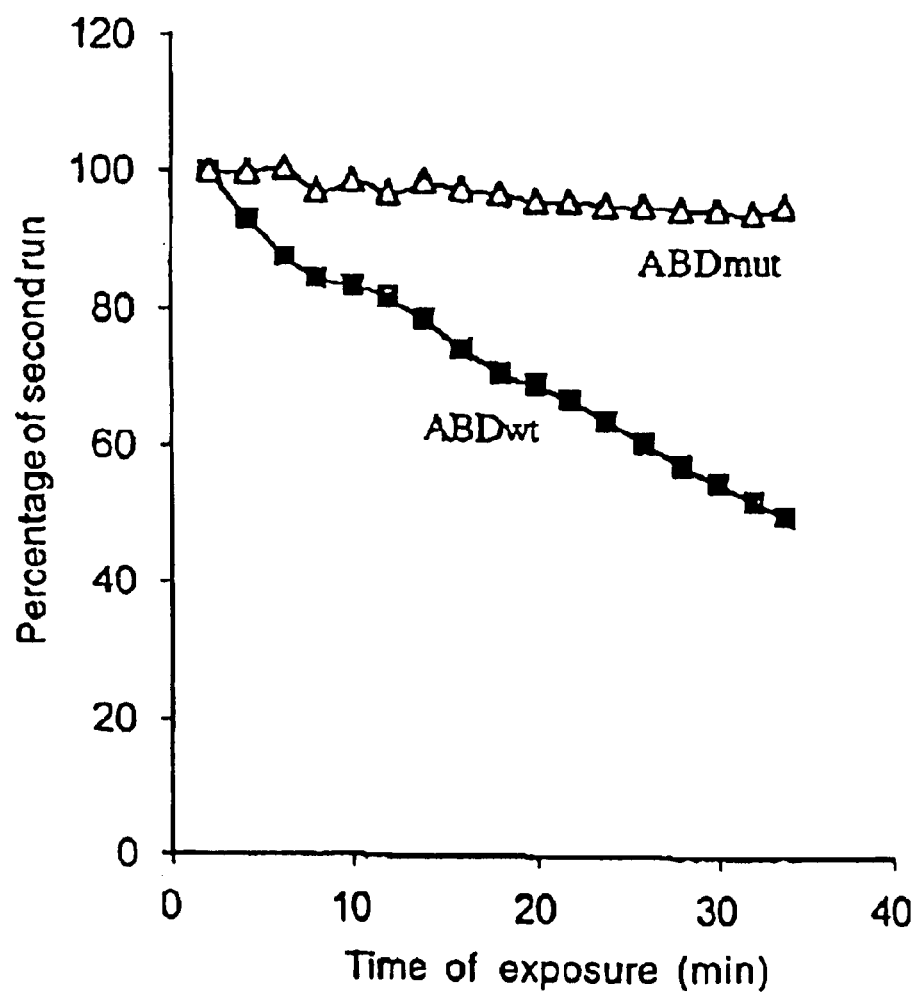
FIG. 6 is a diagram showing the capacity of two affinity matrices, ABDwt and ABDmut respectively, after several rounds of treatment with 0.5M NaOH.

In order to explore the difference between the ABDwt column and the ABDmut column in respect of stability against alkaline treatment, both columns were repeatedly washed with 0.5 M NaOH. By using the AKTA explorer the columns were loaded with HSA, the protein was eluted by lowering the pH (Stahl et al., (1989) supra) and finally both columns were washed with NaOH. This cycle was repeated 15 times and the total time of exposure exceeded 6 hours. The flow rate used was 60 cm/h and the eluted material was collected and analyzed in each round. In FIG. 6 the decrease in capacity is plotted against the NaOH exposure time. As can be seen in the figure, ABDwt is losing the activity quite fast while the mutated variant is keeping the activity throughout the experiment. These results corroborate with the BIACore data, the mutated variant is much more stable against cleaning-in-place (CIP) treatment than the wild type molecule.

EXAMPLE 7

Production and Purification of Z-ABDstab

A frozen E. coli RRIΔM15 culture, harboring the expression vector pTRPZABDstabT1T2 (see Example 8) was used to inoculate 20 ml Tryptic Soy Broth (30 g/l) (Difco, Detroit, Mich., USA) supplemented with 5 g/l yeast extract (Difco) and 50 mg/l kanamycin monsulphate (Labkemi, Stockholm, Sweden). 10 ml of the over night culture was used to inoculate 500 ml of fresh medium. The cells were allowed to grow at 37° C. and expression of the proteins was induced at mid-log phase ($A_{600nm}$=1) by adding 3-β-indole acrylic acid (SIGMA-Aldrich, Stockholm, Sweden) to a final concentration of 25 mg/ml.

After 24 hours the cells were harvested by centrifugation at approximately 5000 g for 10 minutes followed by resuspension in TST buffer (25 mM Tris-HCl pH 7.5, 150 mM NaCl, 1.25 mM EDTA, 0.05% Tween20). The cells were disintegrated by sonication (Vibracell, Sonics & Materials, Danbury, Conn., USA) and centrifuged at 30000 g for 20 minutes. The supernatant was filtered through 0.45 $\mu$m filters (Millipore Corp., Bedford, Mass., USA) and subjected to HSA affinity chromatography (Nygren et al. 1988). The amount of eluted protein was estimated by absorbance measurements using the specific absorption constant, a (L/g*cm), and relevant fractions were lyophilized.

EXAMPLE 8

Genetic Construction of the Fusion Protein Z-ABDstab

Plasmid pTRPZABDstabT1T2 was constructed from pTRPABDmutT1T2. A gene fragment of 233 base pairs, encoding the Z domain was isolated from pRIT45 (Nilsson et al. (1994) Eur. J. Biochem. 224, 1038–108) by XbaI-EcoRI-digestion and ligated into the pTRPABDmutT1T2, which has previously been cut with the same restriction endonucleases. The ligation mixture was used to transform E. coli, strain RRIΔM15. The resulting plasmid contained a gene encoding the fusion protein Z-ABDstab and was denoted pTRPZABDstabT1T2.

The DNA sequences of ABDstab and Z-ABDstab (including the region coding for the 19 amino acid N-terminal tail) are as follows:
ABDstab (SEQ ID NO. 11)
ATGAAAG CAATTTTCGT ACTGAATGCG CAACAC-GATG AAGCCGTAGA CGCGAATTCA TTAGCT-GAAG
CTAAAGTCTT AGCTCTGAGA GAGCTCGACA AATATGGAGT AAGTGACTAT TACAAGGATC TAATCGATAA AGCCAAAACT GTTGAAGGTG TAAAAGCACT GATAGATGAA ATTTTAGCTG CAT-TACCTTA A
Z-ABDstab (SEQ ID NO. 12)
ATGAAAG CAATTTTCGT ACTGAATGCG CAACAC-GATG AAGCCGTAGA CAACAAATTC AACAAA-GAAC
AACAAAACGC GTTCTATGAG ATCTTACATT TAC-CTAACTT AAACGAAGAA CAACGAAACG CCT-TCATCCA AAGTTTAAAA GATGACCCAA GCCAAAGCGC TAACCTTTTA GCAGAAGCTA AAAAGCTAAA TGATGCTCAG GCGCCGAAAG TAGACGCGAA TTCATTAGCT GAAGCTAAAG TCT-TAGCTCT GAGAGAGCTC GACAAATATG GAG-TAAGTGA CTATTACAAG GATCTAATCG ATAAAGCCAA AACTGTTGAA GGTGTAAAAG CACTGATAGA TGAAATTTTA GCTGCATTAC CTTAA

EXAMPLE 9

Genetic Construction of Three Triple Mutants of the ABDmut Domain

Examples 9 and 10 show that it is possible to randomise a surface on the already stabilised ADD-molecule, for example a surface that does not take part in the HSA-binding and thereby create a molecule that is able to bind any target of choice and also retains affinity towards HSA.

Based on the results from an alanine scan experiment to map the binding site for HSA, gene constructs were made encoding ABDmut (see Example 1) domains containing additional alanine substitutions. These were introduced at positions in the domain pointing away from the identified HSA binding motif, which had been located to the first and second helix and the loop in-between. Three different plasmid gene constructs were assembled by PCR based mutagenesis, each encoding ABDmut protein variants containing three alanine substitutions:

pTrpABDmut22-25-26 containing alanine substitutions at positions 22, 25 and 26 of the ABDmut domain;

pTrpABDmut29-30-33 containing alanine substitutions at positions 29, 30 and 33 of the ABDmut domain, and pTrpABDmut54-57-58 containing alanine substitutions at positions 54, 57 and 58 of the ABDmut domain. As a template for the PCR mutagenesis plasmid pTrpABDmutT1T2 was used (see Example 1). The plasmid encodes the gene for ABDmut under transcriptional control of the tryptophan promoter. Exchange of amino acids 22, 25 and 26 for alanine was done by an ordinary PCR mutagenesis using the primer T1T2 (see Example 1) and LIMA 12:

5'-GTAGACGCGA ATTCATTAGC TGCTGCTAAA GCAGCTGCTC TG-3' (LIMA12)(SEQ ID NO. 6)

The PCR mutagenesis for the other two constructs was performed in two steps. In the first PCR amplification the mutations were introduced and in the second PCR, the fragments from the first PCR amplification were mixed and subjected to Taq DNA polymerase assisted double strand DNA synthesis (the same strategy as in FIG. 1), followed by amplification using flanking primers (SOHO8 and T1T2 (see Example 1)). The primers used in the PCR for exchange of amino acids 29, 30 and 33 for alanine were:

5'-ACTCCATATG CGTCGAGCGC TGCCAGAGCT-3' (LIMA13)(SEQ ID NO. 7)

5'-AGCGCTCGAC GCATATGGAG TAAGTGACT-3' (LIMA14)(SEQ ID NO. 8)

For the exchange of amino acids 54, 57 and 58 LIMA15 and LIMA16 were used:

5'-GTGTAGCAGC ACTGGCAGCT GAAATTTTA-3 (LIMA15)(SEQ ID NO. 9)

5'-AAAATTTCAG CTGCCAGTGC TGCTACACCT TCAAC-3' (LIMA16)(SEQ ID NO. 10)

For construction of the plasmid pTrpABDmut22-25-26, the double stranded PCR product was cleaved by restriction endonucleases EcoRI and PstI and for the other two mutants XbaI and PstI was used. The different fragments were ligated into pTrpABDT1T2 restricted with the same enzymes, resulting in a replacement of the wild type ABD domain gene for the three different ABDmut triple mutants. The respective mixtures were used to transform *E. coli*, strain RRIΔM15. After confirming the size of the inserts the sequences were controlled by cycle DNA sequencing (Amersham Pharmacia Biotech, Uppsala, Sweden). The resulting plasmids were denoted pTrpABDmut22-25-26, pTrpABDmut29-30-33, and pTrpABDmut54-57-58, respectively.

The DNA sequences of the three triple mutants are as follows:

ABDmut22-25-26 (SEQ ID NO. 13)

ATGAAAG CAATTTTCGT ACTGAATGCG CAACAC-GATG AAGCCGTAGA CGCGAATTCA TTAGCT-GCTG

CTAAAGCAGC TGCTCTGAGA GAGCTCOACA AATATGGAGT AAGTGACTAT TACAAGGATC TAATCGATAA AGCCAAAACT GTTGAAGGTG TAAAAGCACT GATAGATGAA ATTTTAGCTG CAT-TACCTTA A

ABDmut29-30-33 (SEQ ID NO. 14)

ATGAAAG CAATTTTCGT ACTGAATGCG CAACAC-GATG AAGCCGTAGA CGCGAATTCA TTAGCT-GAAG

CTAAAGTCTT AGCTCTGGCA GCGCTCGACG CATATGGAGT AAGTGACTAT TACAAGGATC

TAATCGATAA AGCCAAAACT GTTGAAGGTG
TAAAAGCACT GATAGATGAA ATTTTAGCTG CAT-
TACCTTA A
ABDmut54-57-58 (SEQ ID NO. 15)
ATGAAAG CAATTTTCGT ACTGAATGCG CAACAC-
GATG AAGCCGTAGA CGCGAATTCA TTAGCT-
GAAG
CTAAAGTCTT AGCTCTGAGA GAGCTCGACA
AATATGGAGT AAGTGACTAT TACAAGGATC
TAATCGATAA AGCCAAAACT GTTGAAGGTG
TAGCAGCACT GGCAGCTGAA ATTTTAGCTG CAT-
TACCTTA A

EXAMPLE 10

Figure 7:
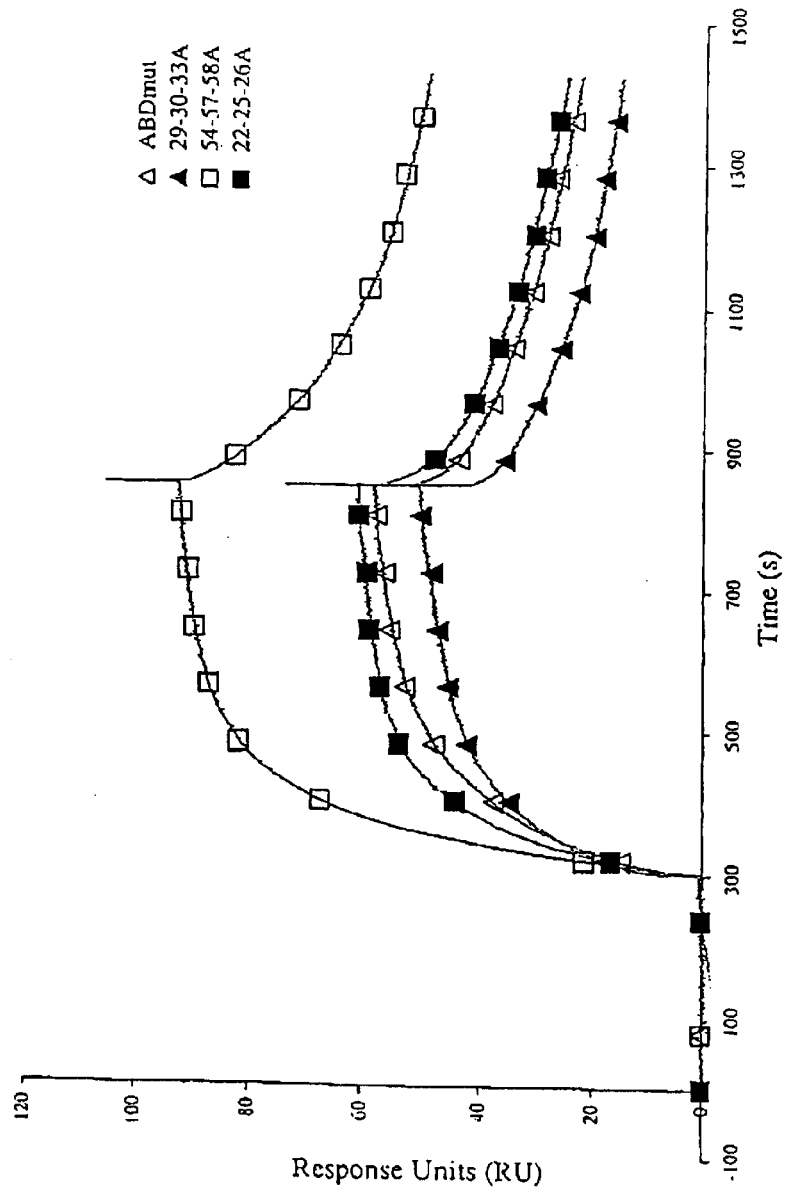
FIG. 7 shows sensorgrams from the Biacore experiment described in Example 10 showing the binding characteristics of ABDmut and the three different triple-mutants thereof, Response Unit (RU) v Time (S); Δ ABDmu; ▲ 29-30-33A; ☐ 54-57-58 A; ■ 22-25-26 A.

HSA-binding Analyses of ABDmut22-25-26,
ABDmut29-30-33, and ABDmut54-57-58 Proteins ABDmut22-25-26, ABDmut29-30-33, and ABDmut54-57-58 proteins were produced and purified as described in Example 2. In order to analyse the binding behaviour of the different triple-mutants a BI core 2000 instrument was used. HSA was immobilised on a sensor chip surface of a CM5 sensor chip by amine coupling to the carboxylated dextran layer. As control, a sensor chip surface containing IgG was used. This coupling was done according to the manufacturers recommendation (Biacore AB). The samples of the three proteins were run through a 0.45 $\mu$m filter and injected over the surface in a random order at a flow rate of 20 $\mu$l/min. The concentration used was 200 nM and all samples were analysed three times. The resulting sensorgrams show that all three triple-mutants retain their ability to bind HSA (FIG. 7). These results indicate that the nine positions (22, 25, 26, 29, 30, 33, 54, 57, 58) investigated in this study should be possible to subject, either simultaneously or in different combinations, to either directed or random mutagenesis in order to identify novel HSA binding ABDwt or ABDmut domains with a second activity, such as binding, catalysis or serving as substrate. In addition, residue 62 could also be used for substitutions.

What is claimed is:

1. A method of affinity separation, comprising the steps of:
   (a) providing a sample containing a target analyte;
   (b) providing a matrix comprising an immobilized protein, said immobilized protein comprising one or more modifications that (i) increase the stability of said protein in alkaline conditions, and (ii) permit said protein to bind to said target analyte, said one or more modifications selected from the group consisting of:
      (1) deleting one or more Asn residues in said protein;
      (2) substituting one or more Asn residues in said protein for an amino acid that is less sensitive to alkaline conditions;
      (3) chemically modifying one or more Asn residues in said protein; and
      (4) combinations thereof;
   (c) contacting said sample and said matrix, wherein said target analyte binds to said immobilized protein; and
   (d) isolating said target analyte from said matrix.

2. The method of claim 1, wherein two or more Asn residues are modified.

3. The method of claim 1, wherein all Asn residues are modified.

4. The method of claim 1, wherein said Asn residues are replaced with an amino acid selected from the group consisting of lysine, aspartic acid, leucine, and combinations thereof.

5. The method of claim 1, wherein said modifications are on the surface of said protein.

6. The method of claim 1, wherein said immobilized protein comprises Albumin-Binding Protein (ABD).

7. The method of claim 6, wherein said modifications in said Albumin-Binding Protein (ABD) are selected from the group consisting of (i) $Asn_{28}$ replaced by Leu, (ii) $Asn_{42}$ replaced by Asp, (iii) $Asn_{48}$ replaced by Asp, (iv) $Asn_{46}$ replaced by Lys, and combinations thereof.

8. The method of claim 1, wherein said immobilized protein is a combinatorial protein.

9. The method of claim 8, wherein said combinatorial protein is derived from an immunoglobulin molecule, staphylococcal protein A (SPA), or a DNA binding protein.

10. The method of claim 8, wherein said combinatorial protein comprises domain Z of the B domain of SPA.

* * * * *

SEQUENCE LISTING

<160> NUMBER OF SEQ ID NOS: 15

<210> SEQ ID NO 1
<211> LENGTH: 65
<212> TYPE: PRT
<213> ORGANISM: Artificial Sequence
<220> FEATURE:
<223> OTHER INFORMATION: Description of Artificial Sequence:mutant of
      wild type ABD

<400> SEQUENCE: 1

Met Lys Ala Ile Phe Val Leu Asn Ala Gln His Asp Glu Ala Val Asp
 1               5                  10                  15

Ala Asn Ser Leu Ala Glu Ala Lys Val Leu Ala Leu Arg Glu Leu Asp
            20                  25                  30

Lys Tyr Gly Val Ser Asp Tyr Tyr Lys Asp Leu Ile Asp Lys Ala Lys
        35                  40                  45

Thr Val Glu Gly Val Lys Ala Leu Ile Asp Glu Ile Leu Ala Ala Leu
    50                  55                  60

Pro
 65

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 2
acgtaaaaag ggtatctaga attatgaaag c                              31

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 3
cagaatcgag actctctcga gctgtttata cc                             32

```
<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence:primer

<400> SEQUENCE: 4
gagagagctc gacaaatatg gagtaagtga ctattacaag gatctaatcg ataaagc        57

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 5
ccgcctactc tcttctaaaa gtcg                                            24

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 6
gtagacgcga attcattagc tgctgctaaa gcagctgctc tg                        42

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 7
actccatatg cgtcgagcgc tgccagagct                                      30

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 8
agcgctcgac gcatatggag taagtgact                                       29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 9
gtgtagcagc actggcagct gaaatttta                                       29

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence:primer
```

```
<400> SEQUENCE: 10
aaaatttcag ctgccagtgc tgctacacct tcaac                                    35

<210> SEQ ID NO 11
<211> LENGTH: 198
<212> TYPE: DNA
<213> ORGANISM: Artificial Sequence
<220> FEATURE:
<223> OTHER INFORMATION: Description of Artificial Sequence:mutant
      version of ABD

<400> SEQUENCE: 11
atgaaagcaa ttttcgtact gaatgcgcaa cacgatgaag ccgtagacgc gaattcatta        60
gctgaagcta aagtcttagc tctgagagag ctcgacaaat atggagtaag tgactattac       120
aaggatctaa tcgataaagc caaaactgtt gaaggtgtaa agcactgat agatgaaatt        180 ttagctgcat taccttaa                                                      198

<210> SEQ ID NO 12
<211> LENGTH: 372
<212> TYPE: DNA
<213> ORGANISM: Artificial Sequence
<220> FEATURE:
<223> OTHER INFORMATION: Description of Artificial Sequence:mutant
      version of ABD

<400> SEQUENCE: 12
atgaaagcaa ttttcgtact gaatgcgcaa cacgatgaag ccgtagacaa caaattcaac        60
aaagaacaac aaaacgcgtt ctatgagatc ttacatttac ctaacttaaa cgaagaacaa       120
cgaaacgcct tcatccaaag tttaaaagat gacccaagcc aaagcgctaa ccttttagca       180
gaagctaaaa agctaaatga tgctcaggcg ccgaaagtag acgcgaattc attagctgaa       240
gctaaagtct tagctctgag agagctcgac aaatatggag taagtgacta ttacaaggat       300
ctaatcgata aagccaaaac tgttgaaggt gtaaaagcac tgatagatga aattttagct       360
gcattacctt aa                                                            372

<210> SEQ ID NO 13
<211> LENGTH: 198
<212> TYPE: DNA
<213> ORGANISM: Artificial Sequence
<220> FEATURE:
<223> OTHER INFORMATION: Description of Artificial Sequence:mutant
      version of ABD

<400> SEQUENCE: 13
atgaaagcaa ttttcgtact gaatgcgcaa cacgatgaag ccgtagacgc gaattcatta        60
gctgctgcta aagcagctgc tctgagagag ctcgacaaat atggagtaag tgactattac       120
aaggatctaa tcgataaagc caaaactgtt gaaggtgtaa agcactgat agatgaaatt        180 ttagctgcat taccttaa                                                      198

<210> SEQ ID NO 14
<211> LENGTH: 198
<212> TYPE: DNA
<213> ORGANISM: Artificial Sequence
<220> FEATURE:
<223> OTHER INFORMATION: Description of Artificial Sequence:mutant
      version of ABD

<400> SEQUENCE: 14
atgaaagcaa ttttcgtact gaatgcgcaa cacgatgaag ccgtagacgc gaattcatta        60
```

```
gctgaagcta aagtcttagc tctggcagcg ctcgacgcat atggagtaag tgactattac    120
aaggatctaa tcgataaagc caaaactgtt gaaggtgtaa aagcactgat agatgaaatt    180
ttagctgcat taccttaa                                                 198

<210> SEQ ID NO 15
<211> LENGTH: 198
<212> TYPE: DNA
<213> ORGANISM: Artificial Sequence
<220> FEATURE:
<223> OTHER INFORMATION: Description of Artificial Sequence:mutant
      version of ABD

<400> SEQUENCE: 15
atgaaagcaa ttttcgtact gaatgcgcaa cacgatgaag ccgtagacgc gaattcatta     60
gctgaagcta aagtcttagc tctgagagag ctcgacaaat atggagtaag tgactattac    120
aaggatctaa tcgataaagc caaaactgtt gaaggtgtag cagcactggc agctgaaatt    180
ttagctgcat taccttaa                                                 198
```